United States Patent [19]
Oliver et al.

[11] Patent Number: 5,806,116
[45] Date of Patent: Sep. 15, 1998

[54] POSITIONING SYSTEM FOR A PATIENT SUPPORT APPARATUS

[75] Inventors: Edward A. Oliver, Cupertino, Calif.; Todd Michael Hauger, Orange City, Iowa

[73] Assignee: Varian Associates, Inc., Palo Alto, Calif.

[21] Appl. No.: 738,429

[22] Filed: Oct. 25, 1996

[51] Int. Cl.⁶ .................................................. A61G 13/10
[52] U.S. Cl. ...................... 5/621; 5/658; 5/424; 378/209; 128/845
[58] Field of Search ............................... 5/601, 621, 622, 5/503.1, 658, 424; 378/177, 209; 128/845, 869

[56] References Cited

U.S. PATENT DOCUMENTS

| | | | |
|---|---|---|---|
| 3,700,229 | 10/1972 | Kurkawa et al. | 5/601 |
| 3,814,419 | 6/1974 | Chapa | 5/601 |
| 3,840,221 | 10/1974 | Hogan | 5/601 |
| 3,981,492 | 9/1976 | Hallman | 5/601 |
| 5,385,119 | 1/1995 | Tarulli | 5/601 X |

*Primary Examiner*—Michael F. Trettel
*Attorney, Agent, or Firm*—Hunter Auyang

[57] ABSTRACT

An accessory has a fixed member and a rotatably supported and eccentrically mounted disk which are each inserted into a corresponding one of a pair of crescent-shaped indentations formed on a panel of a couch top. As the disk is rotated, its center moves towards the fixed member, causing the disk to press against the inner wall of the indentation and locking the accessory to the panel securely and repeatably.

9 Claims, 4 Drawing Sheets

POSITIONING SYSTEM FOR A PATIENT SUPPORT APPARATUS

This invention relates to an integrated system for positioning patients and accessories on a couch top in a precise and repeatable manner for improved treatment of the patient.

BACKGROUND OF THE INVENTION

The current trends in general purpose radiotherapy are directed towards developing more clinically efficient setups and treatments. Consequently, there is a need for devices capable of locating and immobilizing patients that provide precise and repeatable repositioning of the six (three translational and three rotational) degrees of freedom. The devices or accessories also need to be attachable quickly and easily. In addition, there exists a need for flexibility within the locating system to accommodate a broad range of body shapes and treatment sites.

A precise and repeatable indexing system that allows quick and easy attachment is currently not available. Attachment schemes tend to be directed to either a manual method for making minor modifications or non-repeatable clamping arrangements, and in no case are the schemes directly integrated into the couch top design.

Some prior art attachments systems clamp to accessory rails which are found on most radiotherapy couches. Accessory rails are generally fixed lengthwise along the side of the couch top. The rail attachment will generally secure all six degrees of freedom, but not repeatably. Manual adjustment is required to re-establish at least one translational degree and one rotational degree of freedom once the device is removed.

Some devices possess an additional interface between such an accessory rail clamping system and the actual accessory. Pins protruding from either the rail clamping system or the accessory are used to mate with clearance holes. This provides for one translational and two rotational degrees of freedom precisely secured and two translational and one rotational degrees of freedom which are only loosely secured. Although quick and easy to attach, this is not a precise and repeatable locating system as a whole or even at the subsystem level.

Locating systems that actually attach to the treatment surface are essentially custom devices developed by individual hospital personnel. Most use pins protruding from either the couch top surface or the accessory which mate with clearance holes. Again, this also provides for one translational and two rotational degrees of freedom precisely secured and two translational and one rotational degrees of freedom which is only loosely secured. This is not a precise and repeatable locating system, since, by necessity, clearance exists between the hole and the pin.

Capturing two treatment surface edges is another means of locating. Flanges attached to the accessory protrude below the surface of the couch securing one translational and two rotational degrees of freedom precisely and one translational and one rotational degrees of freedom loosely. This leaves one last degree of freedom left unsecured.

Stereotactic head frames, although not used for general purpose radiotherapy, do lock down six degrees of freedom, but they are not quick and easy to attach, since they are bolted in most cases. They do not secure to the treatment surface because a higher precision is required than in general purpose radiotherapy. Attachment is generally to the frame. These devices typically require a separate manual adjustment for precision fine tuning of position by using an external reference such as a laser.

SUMMARY OF THE INVENTION

It is therefore an object of this invention to provide an improved positioning system capable of quickly and easily attaching an accessory device, such as a patient immobilization device, to a couch top for radiotherapy treatments, including diagnostic and simulation processes, requiring precision and repeatability.

The present invention is directed to an integrated positioning system that employs a couch top having a patient support surface and parallel side surfaces. The couch top has indexing points located on the patient support and side surfaces in a symmetrical pattern. The indexing points are an integral part of the couch top, i.e., built-in. The system of the present invention uses a fastening means connected to an accessory device for immobilizing a patient on the couch top. The fastening means has at least two fastening members, which are oriented to releasably engage the couch top at the indexing points. The indexing points are constructed to allow mateable engagement by the fastening members to permit precise and repeatable placement of the device.

A positioning system embodying this invention may be further characterized as comprising a panel on a couch top with integral indexing means and separate accessory device having fastening means for mateably attaching the accessory in a precise and repeatable manner to the panel. The indexing means has at least one pair of indentations. It is preferred that the indexing means provide a series of indentations, which act as pre-defined attachment points for the accessory device. The accessory device has an integral fastening means with at least two fastening members. The accessory device being specifically designed to have a fastening means that mateably attaches to the couch top.

In a preferred embodiment, one of the fastening members is a fixed disk-shaped member and the other is a rotatable, eccentrically mounted disk. The fastening members are aligned and inserted into a pair of indentations. With the eccentricity of the mounted rotatable disk properly selected, the accessory device is securely affixed to the panel by rotating the eccentrically mounted disk around its shaft. A rotating means is attached to the shaft or the rotatable disk. As the rotatable disk is moved towards the fixed disk, with each fastening member positioned at an indentation, the accessory device is locked securely and repeatably to the panel.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings.

DESCRIPTION OF THE PREFERRED EMBODIMENT OF THE INVENTION

Figure 1:
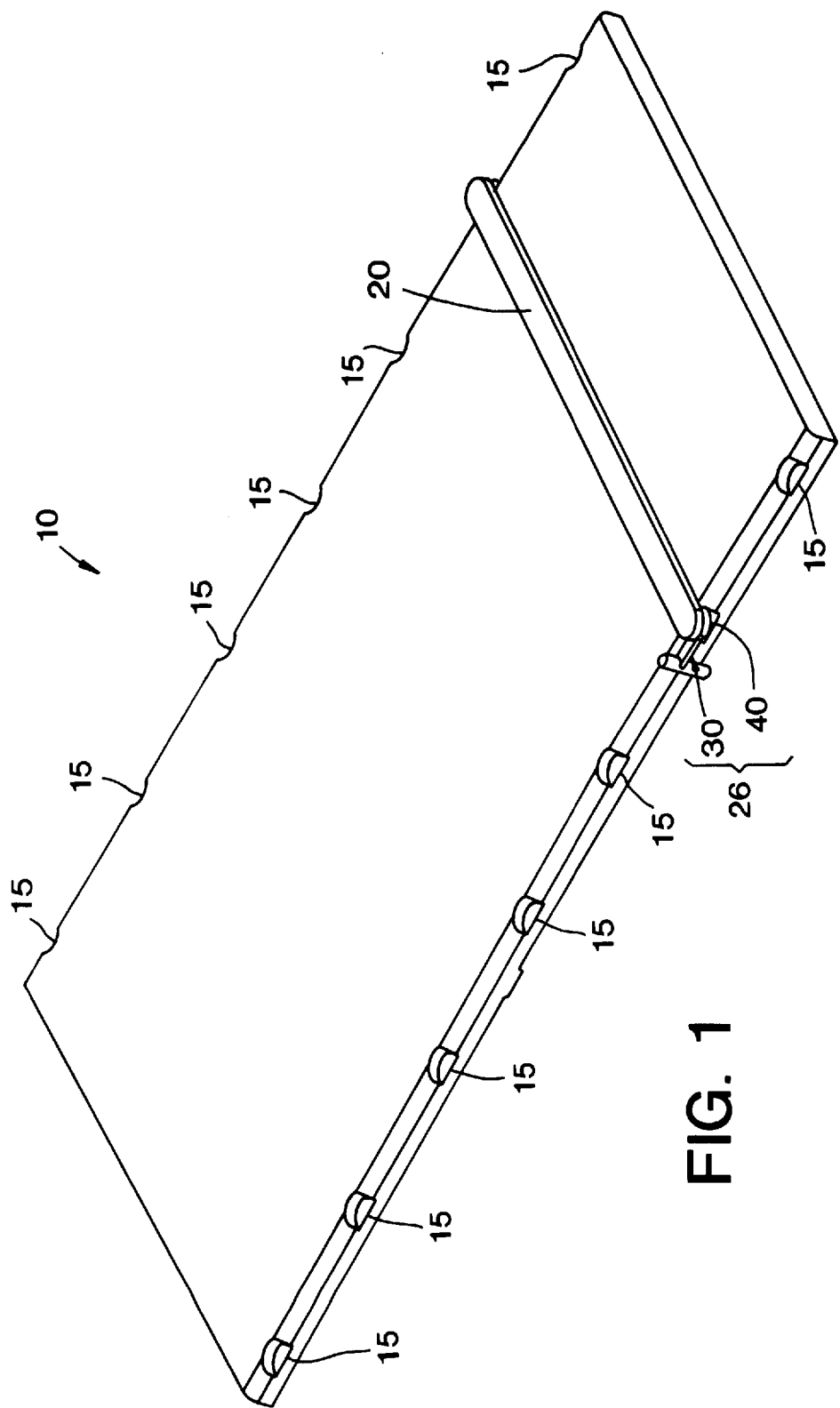
FIG. 1 is a diagonal view of a positioning system embodying this invention with a fastening means in the locked position.
Figure 2:
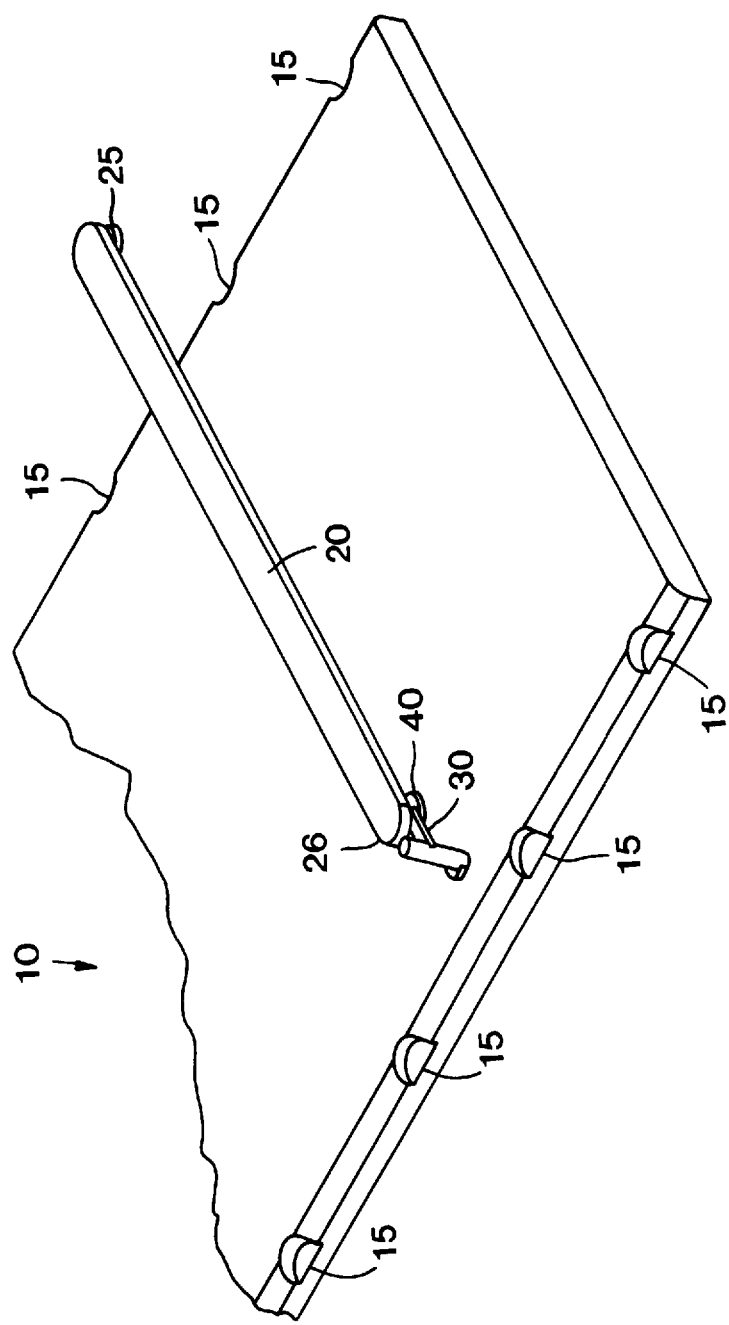
FIG. 2 is a diagonal view of a portion of the positioning system of FIG. 1 with the fastening means is in the unlocked position.
Figure 4:
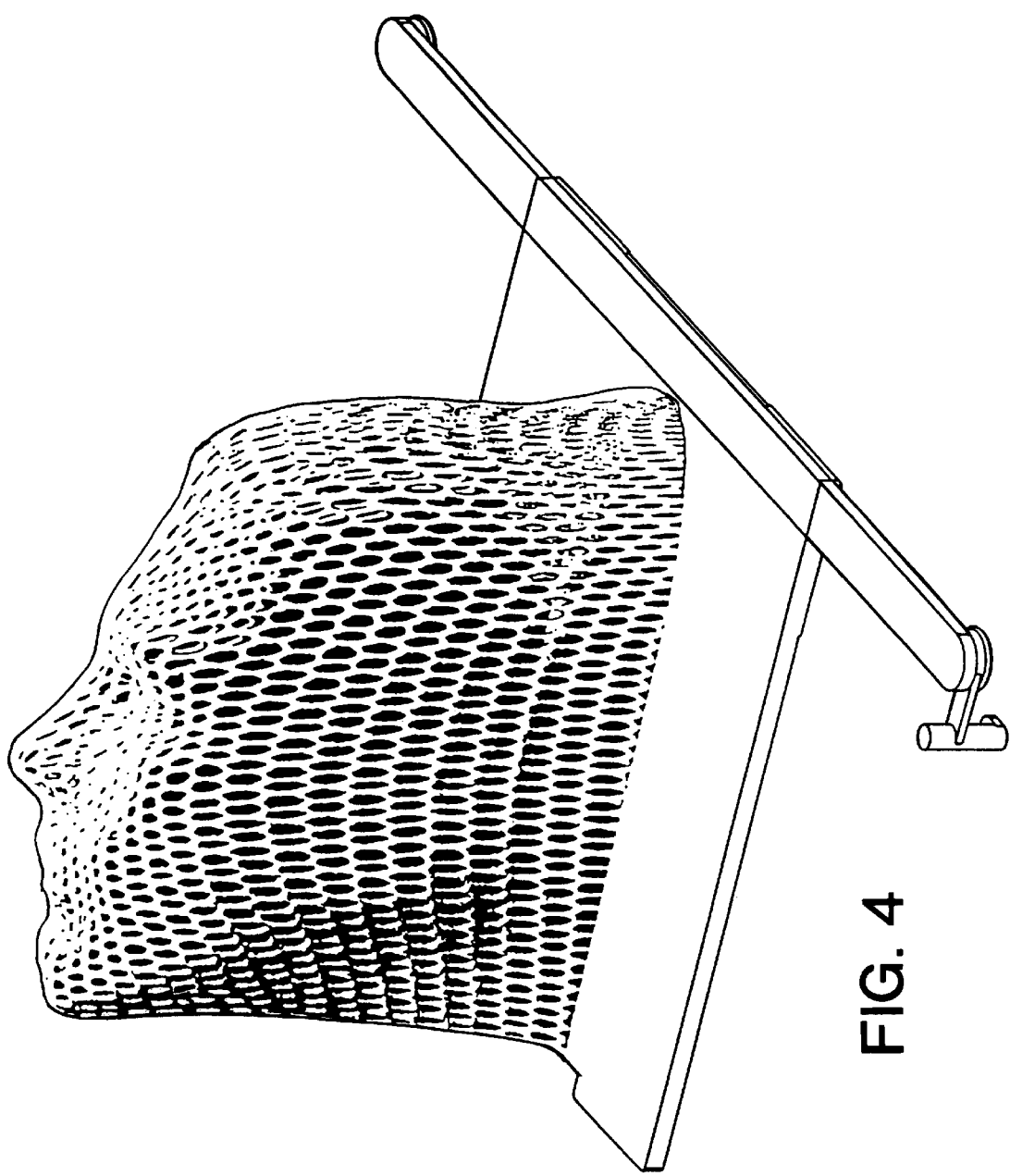
FIG. 4 is a diagram of an accessory mask device with a fastening means.

In the preferred embodiment shown in FIGS. 1 and 2, numeral 10 indicates a generally rectangular panel or top surface of a couch top for supporting a patient during treatment. An accessory device, such as a patient immobilization device (as shown in FIG. 4), is typically used to immobilize the patient, e.g., head, shoulder, torso, etc., to the couch top. The present invention permits the precise and repeatable positioning of the device and hence the patient. The panel 10 is constructed with an indexing means that define specific attachment points as an integral part of the couch top design.

As shown in FIGS. 1 and 2, several pairs of attachment points or indentations 15 are placed on opposite side edges of the panel 10. Each indentation 15 is transversely across the panel surface from a corresponding indentation and are positioned symmetrically around panel 10. According to a preferred embodiment of the invention, the indentations 15 are crescent-shaped and convex facing towards the other of the pair. The indentations 15 are preferably molded into the panel 10, although they may be formed by machining, depending on the exact shape used. The language in the specification, as well as in the claims, is intended to be interpreted broadly. The expression "indentations", for example, is intended to include configurations which may look more like a hole, notch or groove. Therefore, when indentations are used as the indexing means, it should be appreciated that a variety of shapes are possible for the indentations.

Reference numeral 20 indicates a fastening means, which, although not shown as such, is an integral part of the accessory device. The fastening means 20 is attached and secured onto panel 10 by fastening members. Fastening means 20 is shown to be approximately the same length as the width of the rectangular panel 10, which is the same as the distance separating opposite pairs of indentation 15. The preferred embodiment of the fastening means is a flat bar shape. In other embodiments, the fastening means 20 can have, for example, a X-shape (similar to using two bars to form a cross), a Y-shape, a T-shape, a triangle shape, or can be a rectangular or square frame that has fastening members positioned to correspond to the location of the indentations 15. The fastening means should be constructed of a rigid material, e.g., metals or hard plastics. The fastening means will have at least two fastening members. For accessory devices that are sufficiently rigid, the fastening members can be attached directly to the device, i.e., without the use of a fastening means, to secure the device to a couch top.

Figure 3:
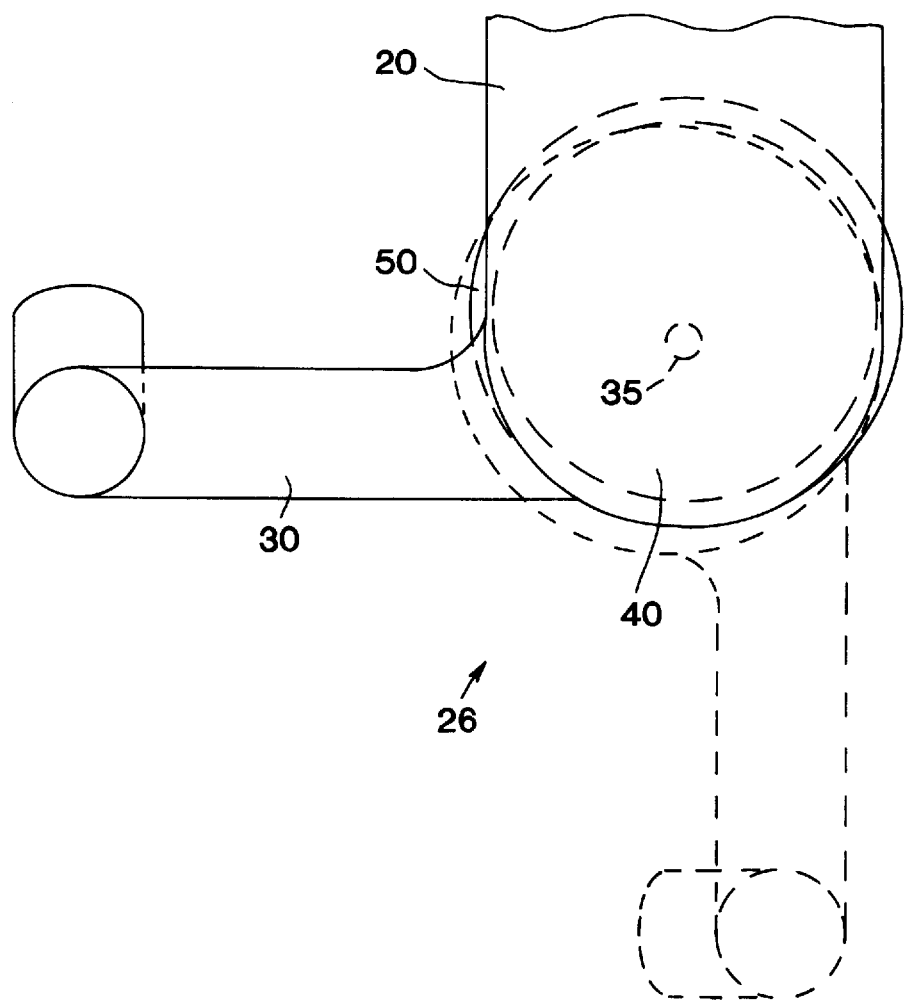
FIG. 3 is an enlarged plan view of a movable fastening member having an eccentrically mounted disk and a lever, as shown in the positioning system of FIGS. 1 and 2.

As shown in FIG. 2, attached to the lower surface of the bar 20 at the ends are fastening members 25 and 26. The fastening member 25 is fixed circular disk-shaped member (herein referred to as the fixed disk) that is designed to mateably fit any of the indentations 15. Fastening member 26 is located at the other end of the bar 20, comprising lever 30 and circular disk 40. Lever 30 is attached to a vertical shaft 35 (as shown in FIG. 3), which is rotatably supported by the bar 20. Circular disk 40 is eccentrically mounted by shaft 35 and serves as a movable locking means. Disk 40 is adapted to rotate with and around the shaft 35 such that, when the lever 30 extends perpendicularly to the direction of extension of the bar 20, as shown by solid line in FIG. 3, the center of the circular disk 40 is on the side of the shaft 35 towards the other end of the bar 20. This embodiment of the fastening means is a simple design that is simple to use and inexpensive to manufacture.

Other fastening members can be used, including well known mechanical devices that are capable of generating a clamping force, such as screw clamps, compression or tension springs, or cam action clamps. In addition, the fastening member can use interference fits, hydraulic pressure, magnetic coupling or combinations thereof.

As shown by the dotted lines in FIG. 3, quick and easy removal of fastening means 20 from the panel 10 is accomplished by rotating the lever 30 by 90 degrees to the direction away from the other end of the bar 20. The eccentrically mounted disk 40 is moved, increasing the distance between the two disks 25 and 40 by a small distance. The attachment is effected by a simple rotation by 90 degrees of the lever 30 from an unlocked position to a locked position. When locked, a clamping force is generated that effectively secures all three translational and three rotational degrees of freedom.

In alternative embodiments, the lever 30 may be replaced by a means for causing the eccentrically mounted disk 40 to be rotated around the shaft 35, including a torque knob (i.e., a device adapted to start slipping after a certain maximum torque is reached). As shown in FIG. 3, an O-ring 50 may be used around the eccentrically mounted disk 40, and the fixed disk 25 as well (not shown), at the interface with the inner walls of the indentations 15. The O-ring 50 will distribute clamping and locking force, reduce surface wear, act to better accommodate variations in spacing with the arcuate inner walls of the indentations 15 and keep the eccentrically mounted disk 40 from slipping by increasing sliding friction. The positioning system of the present invention enables an accessory to be attached to a couch in a definitively precise and repeatable manner.

FIG. 4 is an accessory device used to immobilize the head of a patient. It is made of a thermal plastic.

The invention has been described above with reference to only one example, but the illustrated example is not intended to limit the scope of this invention. Many modifications and variations are possible within the scope of the invention. For example, the fixed disk 25 may be replaced by a fastening member having a different shape, and the indentations 15 need not necessarily be crescent-shaped. Also, a fastening member 26 can be used in place of fixed disk 25. Indentations of any shape capable of properly accepting and engaging fastening members can serve the purpose of this invention, provided they are properly matched.

What is claimed is:

1. A positioning system for use in patient treatment comprising:

a panel of a couch top with an integral indexing means, said indexing means comprising at least one pair of indentations;

an accessory device having a fastening means for permitting removable attachment of said device to said panel, said fastening means having at least a first and second fastening members, said first fastening member having a fixed disk member that is mateably positioned at one of said indentations, said second fastening member having a rotatable disk member that is eccentrically mounted to a shaft and mateable positioned at the other of said indentations, said fixed disk member and said rotatable disk being separated by a distance which corresponds with the separation between said pair of indentations; and rotating means for moving said rotatable disk around said shaft to mate said first and second fastening members with said pair of indentations causing said device to be locked securely and repeatably to said panel.

2. The positioning system of claim 1 wherein said panel has a plurality of pairs of indentations on side edges thereof.

3. The positioning system of claim 1 wherein said rotating means comprises a lever which extends perpendicularly from said shaft.

4. The positioning system of claim 1 wherein said fastening means is an elongated bar having said fixed disk member attached to one end of said bar and having said rotatable disk and said shaft mounted to said bar at the other end thereof.

5. The positioning system of claim 1 wherein said indentations are each crescent-shaped, said pair of indentations being convex towards each other.

6. An integrated positioning system comprising:

a couch top having a patient support surface and parallel side surfaces;

indexing points located on said patient support and side surfaces of said couch top in a symmetrical pattern, said indexing points being integral parts of said couch top; and a fastening means connected to a positioning device for securing a patient to said couch top, said fastening means having at least two fastening members;

said fastening members being oriented to releasably engage said couch top at said indexing points by exerting a clamping force that locks said positioning device at said indexing point thereby permitting precise and repeatable placement of said positioning device.

7. A positioning system for use in radiotherapy comprising:

a panel of a couch top with an integral indexing means, said indexing means providing a series of pre-defined attachment points; and an accessory device having at least a first and second fastening members for permitting the removable attachment of said device to said panel, with each said fastening member being mateably positioned at one of said series of pre-defined attachment points and at least one of said fastening members being mechanically movable to engage said panel in a precise and repeatable manner.

8. The positioning system of claim 7 wherein said first fastening member further comprises a locking means.

9. An accessory device for use in a patient positioning system comprising:

a means for immobilizing a patient;

a fastening means for permitting removable attachment of said device to a panel of a couch top with an integral indexing means, said indexing means having at least one pair of attachment points; and said fastening means having at least a first and second fastening members, said first and second fastening members exerting a clamping force at said attachment points of said couch top to lockably position said accessory device.

* * * * *